(12) United States Patent
Maile et al.

(10) Patent No.: US 10,213,610 B2
(45) Date of Patent: Feb. 26, 2019

(54) COMMUNICATIONS IN A MEDICAL DEVICE SYSTEM WITH LINK QUALITY ASSESSMENT

(71) Applicant: CARDIAC PACEMAKERS, INC., St. Paul, MN (US)

(72) Inventors: Keith R. Maile, New Brighton, MN (US); Brendan E. Koop, Ham Lake, MN (US); Brian L. Schmidt, White Bear Lake, MN (US); Michael J. Kane, Roseville, MN (US); Jacob M. Ludwig, Isanti, MN (US); Jeffrey E. Stahmann, Ramsey, MN (US); Lance E. Juffer, Lino Lakes, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 137 days.

(21) Appl. No.: 15/070,013

(22) Filed: Mar. 15, 2016

(65) Prior Publication Data

US 2016/0271406 A1    Sep. 22, 2016

Related U.S. Application Data

(60) Provisional application No. 62/134,726, filed on Mar. 18, 2015.

(51) Int. Cl.
*A61N 1/00*     (2006.01)
*A61N 1/372*    (2006.01)
(Continued)

(52) U.S. Cl.
CPC ........ *A61N 1/37288* (2013.01); *A61B 5/0002* (2013.01); *A61B 5/0024* (2013.01);
(Continued)

(58) Field of Classification Search
USPC .......................................................... 607/60
See application file for complete search history.

(56) References Cited

U.S. PATENT DOCUMENTS 3,835,864 A    9/1974  Rasor et al.
3,943,936 A    3/1976  Rasor et al.
(Continued)

FOREIGN PATENT DOCUMENTS

AU    2008279789 B2    10/2011
AU    2008329620 B2    5/2014
(Continued)

OTHER PUBLICATIONS

US 8,886,318, 11/2014, Jacobson et al. (withdrawn)
(Continued)

*Primary Examiner* — Nicole F Johnson
(74) *Attorney, Agent, or Firm* — Seager, Tufte & Wickhem LLP

(57) ABSTRACT

Methods and devices for testing and configuring implantable medical device systems. A first medical device and a second medical device communicate with one another using test signals configured to provide data related to the quality of the communication signal to facilitate optimization of the communication approach. Some methods may be performed during surgery to implant one of the medical devices to ensure adequate communication availability.

10 Claims, 15 Drawing Sheets

(51) Int. Cl.
*A61B 5/00* (2006.01)
*A61B 5/024* (2006.01)
*A61B 5/02* (2006.01)
*A61B 5/08* (2006.01)
*A61B 5/11* (2006.01)
*A61N 1/362* (2006.01)
*A61N 1/375* (2006.01)
*A61N 1/39* (2006.01)
*H04B 13/00* (2006.01)

(52) U.S. Cl.
CPC .............. *A61B 5/0028* (2013.01); *A61B 5/02* (2013.01); *A61B 5/024* (2013.01); *A61B 5/08* (2013.01); *A61B 5/11* (2013.01); *A61B 5/6869* (2013.01); *A61B 5/7221* (2013.01); *A61N 1/362* (2013.01); *A61N 1/3756* (2013.01); *A61N 1/37217* (2013.01); *A61N 1/37252* (2013.01); *A61N 1/3962* (2013.01); *H04B 13/005* (2013.01); *A61N 1/3727* (2013.01); *A61N 1/37205* (2013.01); *A61N 1/37247* (2013.01)

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,466,246 A | 11/1995 | Silvian |
| 5,468,254 A | 11/1995 | Hahn et al. |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,591,214 A | 1/1997 | Lu |
| 5,620,466 A | 4/1997 | Haefner et al. |
| 5,634,938 A | 6/1997 | Swanson et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras et al. |
| 5,954,757 A | 9/1999 | Gray |
| 5,978,713 A | 11/1999 | Prutchi et al. |
| 5,991,660 A | 11/1999 | Goyal |
| 5,999,848 A | 12/1999 | Gord et al. |
| 5,999,857 A | 12/1999 | Weijand et al. |
| 6,026,320 A | 2/2000 | Carlson et al. |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,080,187 A | 6/2000 | Alt et al. |
| 6,083,248 A | 7/2000 | Thompson |
| 6,106,551 A | 8/2000 | Crossett et al. |

(56) References Cited

U.S. PATENT DOCUMENTS

| | | |
|---|---|---|
| 6,115,636 A | 9/2000 | Ryan |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,298,271 B1 | 10/2001 | Weijand |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,110,824 B2 | 9/2006 | Amundson et al. |
| 7,120,504 B2 | 10/2006 | Osypka |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,790 B2 | 4/2007 | Thompson et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Heltinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |

(56) References Cited

U.S. PATENT DOCUMENTS

| | | |
|---|---|---|
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,792,588 B2 | 9/2010 | Harding |
| 7,797,059 B1 | 9/2010 | Bornzin et al. |
| 7,801,596 B1 | 9/2010 | Fischell et al. |
| 7,809,438 B2 | 10/2010 | Echt et al. |
| 7,840,281 B2 | 11/2010 | Kveen et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,204,595 B2 | 6/2012 | Pianca et al. |
| 8,204,605 B2 | 6/2012 | Hastings et al. |

(56) References Cited

U.S. PATENT DOCUMENTS

| | | |
|---|---|---|
| 8,209,014 B2 | 6/2012 | Doerr |
| 8,214,043 B2 | 7/2012 | Matos |
| 8,224,244 B2 | 7/2012 | Kim et al. |
| 8,233,985 B2 | 7/2012 | Bulkes et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,527,068 B2 | 9/2013 | Ostroff |
| 8,532,790 B2 | 9/2013 | Griswold |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,773 B2 | 5/2014 | Willis et al. |
| 8,738,147 B2 | 5/2014 | Hastings et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,500 B2 | 12/2014 | Smith et al. |
| 8,903,513 B2 | 12/2014 | Ollivier |
| 8,914,131 B2 | 12/2014 | Bomzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bomzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,144 B2 | 1/2016 | Greene et al. |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |

(56) References Cited

U.S. PATENT DOCUMENTS

| | | |
|---|---|---|
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0041866 A1 | 3/2003 | Linberg et al. |
| 2003/0088278 A1 | 5/2003 | Bardy et al. |
| 2003/0097153 A1 | 5/2003 | Bardy et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |

(56) References Cited

U.S. PATENT DOCUMENTS

| | | |
|---|---|---|
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114197 A1 | 5/2010 | Burnes et al. |
| 2010/0114209 A1 | 5/2010 | Krause et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160557 A1 | 6/2011 | Cinbis et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109258 A1 | 5/2012 | Cinbis et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1* | 2/2013 | Smith ............. A61N 1/372 607/4 |
| 2013/0053915 A1 | 2/2013 | Holmstrom et al. |
| 2013/0053921 A1 | 2/2013 | Bonner et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0046690 A1* | 2/2014 | Gunderson ......... G06F 19/3418 705/3 |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |

(56) References Cited

U.S. PATENT DOCUMENTS

| | | |
|---|---|---|
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0257324 A1 | 9/2014 | Fain |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0121127 A1 | 5/2016 | Klimovitch et al. |
| 2016/0121128 A1 | 5/2016 | Fishier et al. |
| 2016/0121129 A1 | 5/2016 | Persson et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Spickler et al., "Totally Self-Contained Intracardiac Pacemaker," Journal of Electrocardiology, vol. 3(3&4): 324-331, 1970.

"Instructions for Use System 1, Leadless Cardiac Pacemaker (LCP) and Delivery Catheter," Nanostim Leadless Pacemakers, pp. 1-28, 2013.

International Search Report and Written Opinion PCT/US2016/022456 dated Jun. 2, 2016.

* cited by examiner

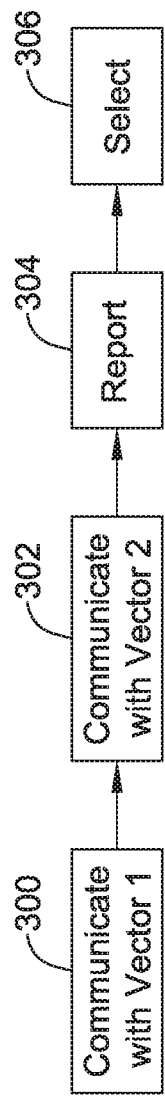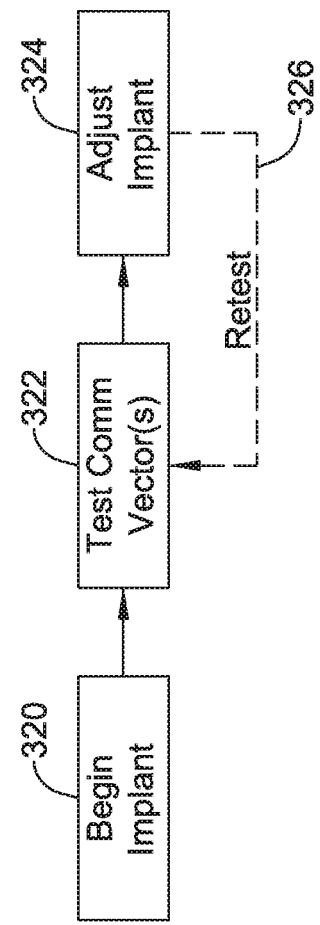

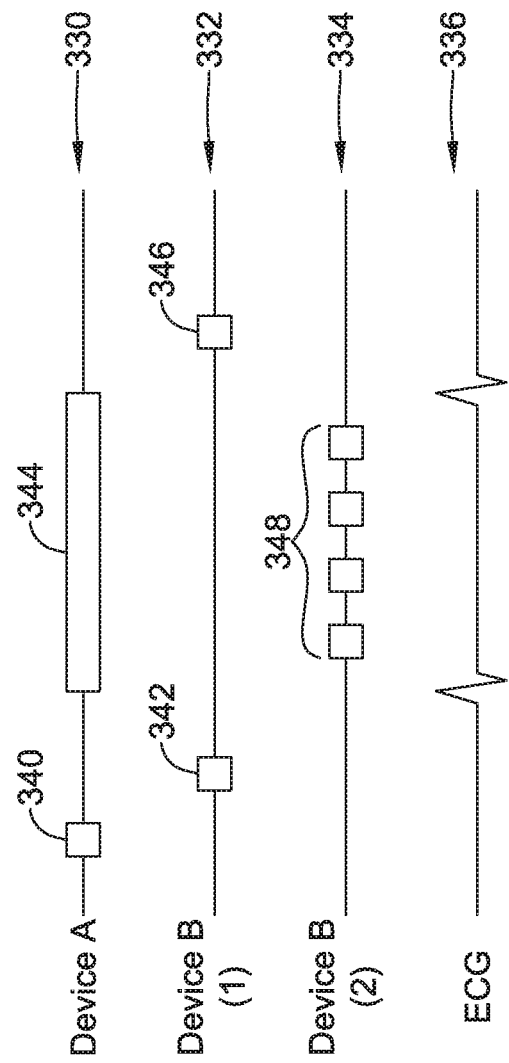

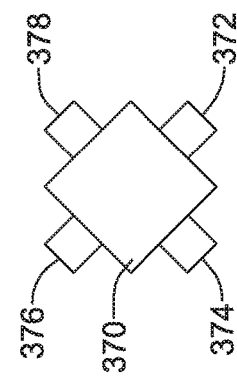
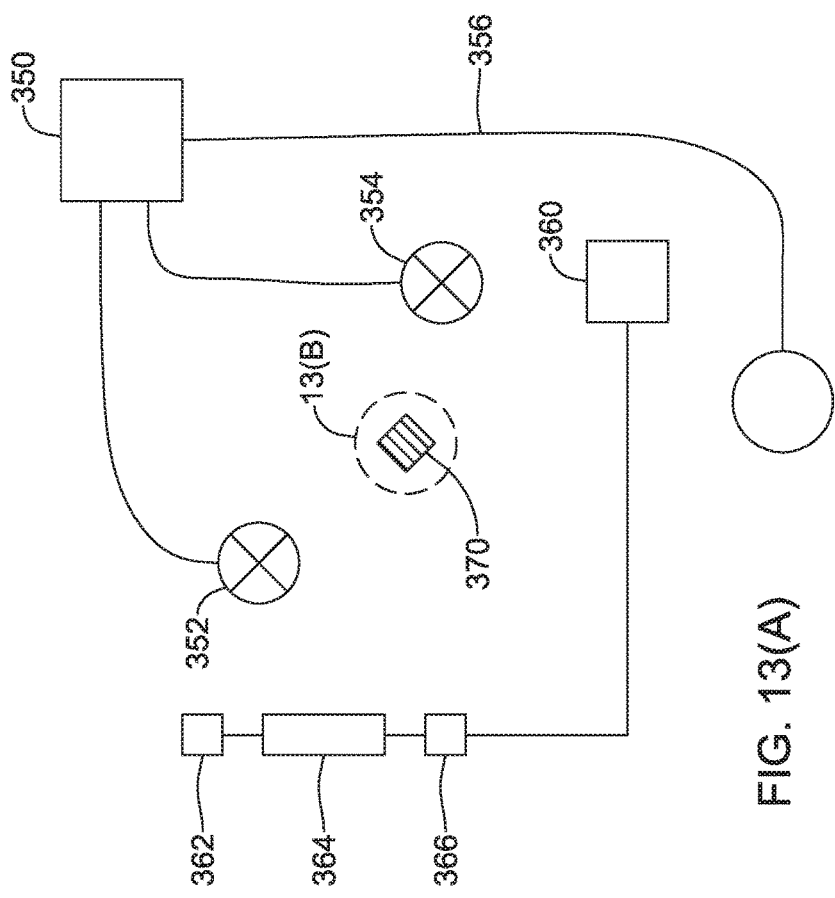
FIG. 13(B)
FIG. 13(A)

ated herein# COMMUNICATIONS IN A MEDICAL DEVICE SYSTEM WITH LINK QUALITY ASSESSMENT

CROSS REFERENCE TO RELATED APPLICATIONS

The present application claims the benefit of and priority to U.S. Provisional Patent Application No. 62/134,726, and titled COMMUNICATIONS IN A MEDICAL DEVICE SYSTEM WITH LINK QUALITY ASSESSMENT, filed Mar. 18, 2015, the disclosure of which is incorporated herein by reference.

TECHNICAL FIELD

The present disclosure generally relates to medical devices, and more particularly to communications between implantable medical devices.

BACKGROUND

Various active implantable devices are available or in development for treating and/or diagnosing numerous ailments. Some examples include cardiac assist devices, pacemakers, defibrillators, cardiac monitors, neurostimulation and neuromodulation systems, drug and medication pumps, and others. A patient may have multiple implanted devices and may benefit in some circumstances by enabling such devices to communicate with one another. Because these implantable devices are generally reliant on battery power, communication between devices should be designed for efficiency and to limit power consumption.

SUMMARY

The present disclosure relates generally to systems and methods for managing communication strategies using link quality assessment.

A first example is an implantable medical device comprising means for communicating by conducted communication with at least a second implantable medical device; means for setting the means for communicating into a continuing receive mode for analyzing a first signal received from the second implantable medical device and a second signal received from the second implantable medical device; means for analyzing the first signal and the second signal as received by the means for communicating; and means for generating an output communication indicating a result of the analysis of the first signal and the second signal.

A second example takes the form of the implantable medical device of the first example, wherein the means for analyzing the first signal and the second signal is operable by receiving and analyzing a biological signal from a patient to identify events in the biological signal to generate a marker set; and annotating the first signal and the second signal using the marker set.

A third example takes the form of the implantable medical device of the second example, wherein the biological signal is a cardiac signal and the events are components of the cardiac cycle.

A fourth example takes the form of the implantable medical device of any of the first three examples, wherein the continuing receive mode includes a period for receiving at least one of the first signal and the second signal for a duration which exceeds a recurring biological cycle of a patient. A fifth example takes the form of the implantable medical device of the fourth example wherein the recurring biological cycle is a cardiac cycle. A sixth example takes the form of the implantable medical device of the fourth example wherein the recurring biological cycle is a respiration cycle.

A seventh example takes the form of the implantable medical device of any of the first six examples wherein the means for generating an output communication is operable to generate an output communication signaling: a preference for the first signal; a preference for the second signal; or an indication that neither of the first signal nor the second signal is suitable.

An eighth example takes the form of a medical system comprising an implantable medical device as in the seventh example and an external programmer for communication with the implantable medical device, the external programmer including a user interface, wherein the implantable medical device means for generating an output communication is operable to send an output communication for receipt by the external programmer; and wherein the external programmer is configured to indicate to a user if the implantable medical device generated an indication that neither of the first signal nor the second signal is suitable, and to suggest that the user modify the position of the implantable medical device.

A ninth example takes the form of a system as in the eighth example wherein the implantable medical device and external programmer are configured to communicate in real-time to indicate to the physician changes to a conducted communication signal received by the implantable medical device as the implantable medical device position is adjusted by the physician.

A tenth example takes the form of a medical system comprising a first implantable medical device as in the seventh example, a second implantable medical device, and an external programmer for communication with at least one of the first and second implantable medical devices, wherein the first implantable medical device is configured to receive the first signal and the second signal from the second implantable medical device and generate the output communication for receipt by the second implantable medical device, and the second implantable medical device is configured to communicate to the external programmer.

An eleventh example takes the form of a medical system comprising a first implantable medical device as in the seventh example and a second implantable medical device configured to generate conducted communication signals to the first implantable medical device, the second implantable medical device comprising at least first, second and third electrodes for generating the conducted communication to yield at least first and second conducted communication vectors, wherein the second implantable medical device is configured to generate the first signal using a first conducted communication vector, and to generate the second signal using a second conducted communication vector.

A twelfth example takes the form of a medical system comprising a first implantable medical device as in any of the first six examples, a second implantable medical device, and an external programmer for communication with the first and second implantable medical devices, wherein the first implantable medical device is configured to receive the first and second signals from the second implantable medical device and generate the output communication to the external programmer.

A thirteenth example takes the form of a medical system as in any of the tenth to twelfth examples wherein the first implantable medical device is configured as a leadless cardiac pacemaker for implantation entirely within the heart of a patient, and the second implantable medical device is configured as a subcutaneous-only implantable defibrillator.

A fourteenth example takes the form of the implantable medical device of any of the first seven examples further comprising therapy circuitry for providing pacing output and wherein the implantable medical device is configured as a leadless cardiac pacemaker for implantation entirely within the heart of a patient.

A fifteenth example takes the form of an implantable medical device comprising means for communicating by conducted communication with at least a second implantable medical device, at least first, second and third electrodes configured for conducted communication with the second implantable medical device such that at least first and second conducted communication vectors are available for use by the communication means, means for setting the means for communicating to a continuing transmit mode for using the first conducted communication vector to generate an output, and then using the second conducted communication vector to generate an output; means for determining, from information provided back to the implantable medical device, which, if any, of the first conducted communication vector and second conductive communication vector is to be used for delivering conducted communication messages to the second implantable medical device; and means for setting a default conducted communication vector for use by the means for communicating.

A sixteenth example is a method of performing a diagnostic test in an implantable medical device system comprising: generating a first conducted signal from a first medical device intended for receipt by a second medical device comprising an output pattern for a selected period; receiving the conducted signal by a second medical device and calculating a parameter of the first conducted signal as received; wherein the selected period exceeds an expected or detected length of a recurring biological cycle.

A seventeenth example takes the form of a method as in the sixteenth example, wherein the recurring biological cycle is a cardiac cycle. An eighteenth example takes the form of a method as in the sixteenth example wherein the recurring biological signal is a respiration cycle.

A nineteenth example takes the form of a method as in any of the sixteenth to eighteenth examples wherein the first medical device comprises at least three electrodes configured to output a conducted signal and the first conducted signal is generated by a first combination of electrodes, the method further comprising generating a second conducted signal using a second combination of electrodes, receiving the second conducted signal and calculating the parameter for the second conducted signal. A twentieth example takes the form of a method as in the nineteenth example, further comprising comparing the parameter as calculated for the first conducted signal as received to the parameter as calculated for the second conducted signal.

A twenty-first example is a method comprising performing a method as in any of the sixteenth to twentieth examples while a patient assumes a first posture, and repeating the same method while the patient assumes a second posture.

A twenty-second example is a method of configuring communication between implantable medical devices comprising: in a first implantable device having a plurality of electrodes configured for outputting a conducted signal, generating a first conducted signal using a selected pair of electrodes; in a second implantable device, receiving and analyzing the first conducted signal; in the second implantable device, communicating a second signal related to an outcome of the analysis of the first conducted signal while the first conducted signal is being received.

A twenty-third example takes the form of a method as in the twenty-second example, further comprising receiving the second signal in the first implantable device while the first conducted signal is still being generated. A twenty-fourth example takes the form of a method as in either of the twenty-second or twenty-third examples, wherein the second signal is a conducted signal received by the first implantable device using a different pair of electrodes than the pair used for generating the first conducted signal. A twenty-fifth example takes the form of a method as in either of the twenty-second or twenty-third examples, wherein the second signal is not a conducted signal. A twenty-sixth example takes the form of a method as in the twenty-second example, further comprising receiving the second signal with an external medical device configured for communication with at least one of the first implantable device and the second implantable device.

A twenty-seventh example is a method of configuring communication between implantable medical devices during an implantation procedure of a first medical device in a patient in whom a second medical device is already implanted, the method comprising: during an implantation procedure for the first medical device, testing communication between the first medical device and the second medical device; determining that communication is suboptimal; and in response to determining that communication is suboptimal, adjusting an orientation of the first medical device.

A twenty-eighth example takes the form of a method as in the twenty-seventh example, wherein at least one of the first medical device and the second medical device is configured for communication with an external programmer, the method further comprising obtaining a feedback signal from the external programmer which indicates in real time a quality of a communication link between the first medical device and the second medical device.

A twenty-ninth example takes the form of a method as in either of the twenty-seventh or twenty-eighth examples wherein the first medical device is a leadless cardiac pacemaker and the second medical device is a subcutaneous implantable cardioverter defibrillator. A thirtieth example takes the form of a method as in either of the twenty-seventh or twenty-eighth examples wherein the first medical device is a leadless cardiac pacemaker (LCP) which is implanted by advancing an implantation catheter to a desired location and then securing the LCP at the desired location and decoupling the implantation catheter from the LCP, wherein the step of testing communication is performed while the LCP is coupled to the implantation catheter and before the LCP is secured at the desired location.

A thirty-first example is a method of operation in an implantable medical device system comprising an external programmer and first implantable medical device and a second implantable medical device, the method being configured for performance communication quality monitoring during a procedure to implant the second medical device while the first medical device is already implanted, the method comprising: the first medical device generating a communication test signal prior to completion of placement of the second medical device during the procedure to implant the second medical device; the second medical device receiving and analyzing the communication test signal from the first medical device; the second medical device generating an output indicating a quality of the communication test signal as received; the programmer providing an indication to a physician performing the implantation procedure related to the quality of the communication test signal as received by the second medical device.

A thirty-second example takes the form of a method as in the thirty-first example wherein the step of the second medical device generating an output indicating a quality of the communication test signal comprises the second medical device communicating to the programmer in real time, such that the step of the programmer providing an indication is performed in real time. A thirty-third example takes the form of a method as in the thirty-first example, wherein the step of the second medical device generating an output indicating a quality of the communication test signal comprises the second medical device communicating back to the first medical device and the first medical device communicating to the programmer to facilitate the programmer providing the indication to the physician.

A thirty-fourth example takes the form of a method as in any of the thirty-first to thirty-third examples wherein the first and second medical devices are each leadless cardiac pacemakers. A thirty-fifth example takes the form of a method as in any of the thirty-first to thirty-third examples wherein the first medical device is a subcutaneous implantable cardioverter defibrillator and the second medical device is a leadless cardiac pacemaker.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIGS. 9-10 are flow diagrams for illustrative methods;

FIG. 11 is another diagram illustrating communications signals and test signals relative to biological signals;

FIGS. 13A-13B show an implanted system and a detail view of a particular device.

Figure 1:
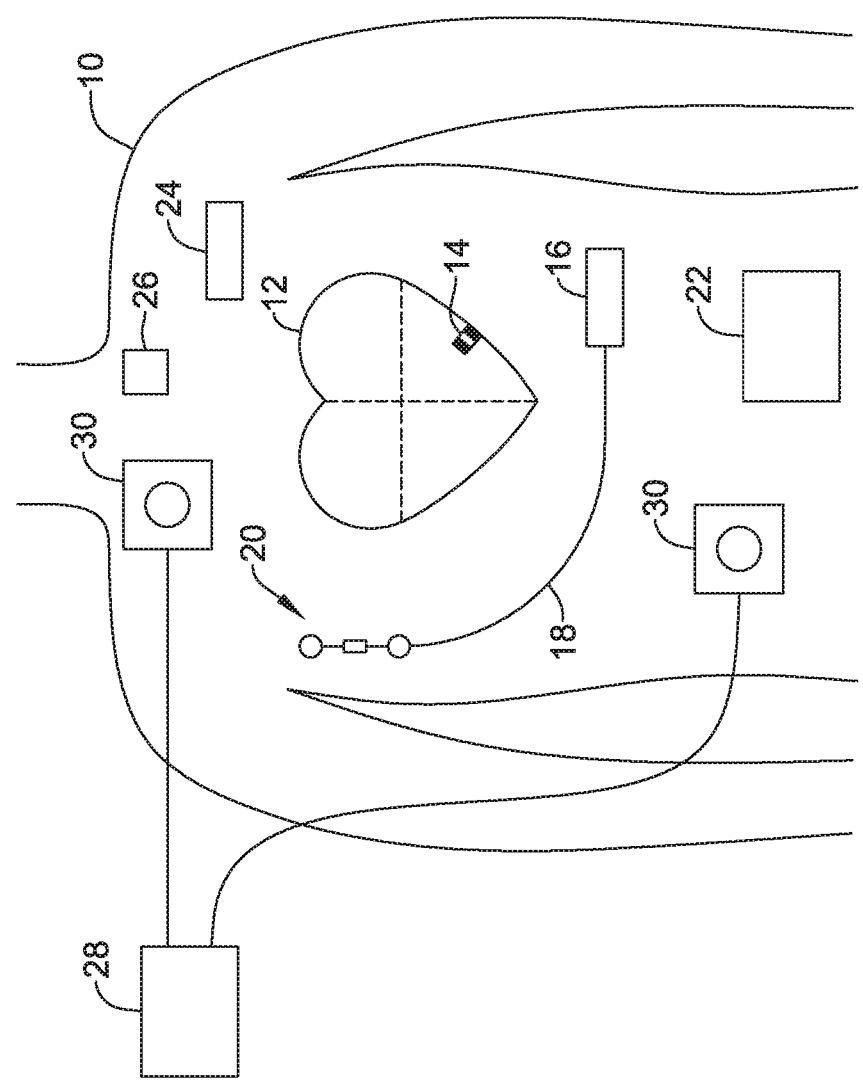
FIG. 1 illustrates a patient having a plurality of implantable medical devices.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

FIG. 1 illustrates a patient having a plurality of implantable medical devices. A patient, 10 is shown having a leadless cardiac pacemaker (LCP) 14 implanted inside the heart 12. A subcutaneous implantable defibrillator (SICD) 16 having a left axillary canister and lead 18 extending to electrodes 20 is also shown. The patient may also have an insulin pump 22, a pain pump 24 for delivering pain medication to the shoulder, and/or a nerve stimulator 26 having a lead (not shown) extending to the neck or head.

Other devices could be substituted for those shown in FIG. 1, and the positions shown for each device are not intended to be limiting. Some additional or alternative examples include other pacemakers or defibrillators, such as those with transvenous, intracardiac, epicardial, or substernal electrodes, for example, a cardiac monitor, left ventricular assist device, spinal cord stimulator, vagus nerve stimulator, gastric electric stimulator, sacral nerve stimulator, and/or any other implantable medical device.

These various systems may be interrogated by an external device or a "programmer" 28, which may optionally use one or more skin electrodes 30 to assist with communication to an implanted device. Skin electrodes 30 may be used for conducted communication with an implantable device. As used herein, conducted communication is communication via electrical signals which propagate via patient tissue and are generated by more or less ordinary electrodes. By using the existing electrodes, conducted communication does not rely on an antenna and an oscillator/resonant circuit having a tuned center frequency common to both transmitter and receiver.

For other communication approaches such as RF or inductive communication, the programmer 28 may instead use a programming wand or may have an antenna integral with the programmer 28 housing for communication. Though not shown in detail, the programmer 28 may include any suitable user interface, including a screen, buttons, keyboard, touchscreen, speakers, and various other features widely known in the art.

It is unlikely a single patient 10 would have all of the different systems implanted as shown in FIG. 1. For purposes of the present invention, it is assumed that a patient may have at least two implantable systems simultaneously, and it may be beneficial to facilitate communication between the at least two implantable systems. The mode for communication between two implanted systems may be conducted communication, though other approaches (optical, acoustic, inductive or RF, for example) could be used instead.

Figure 2:
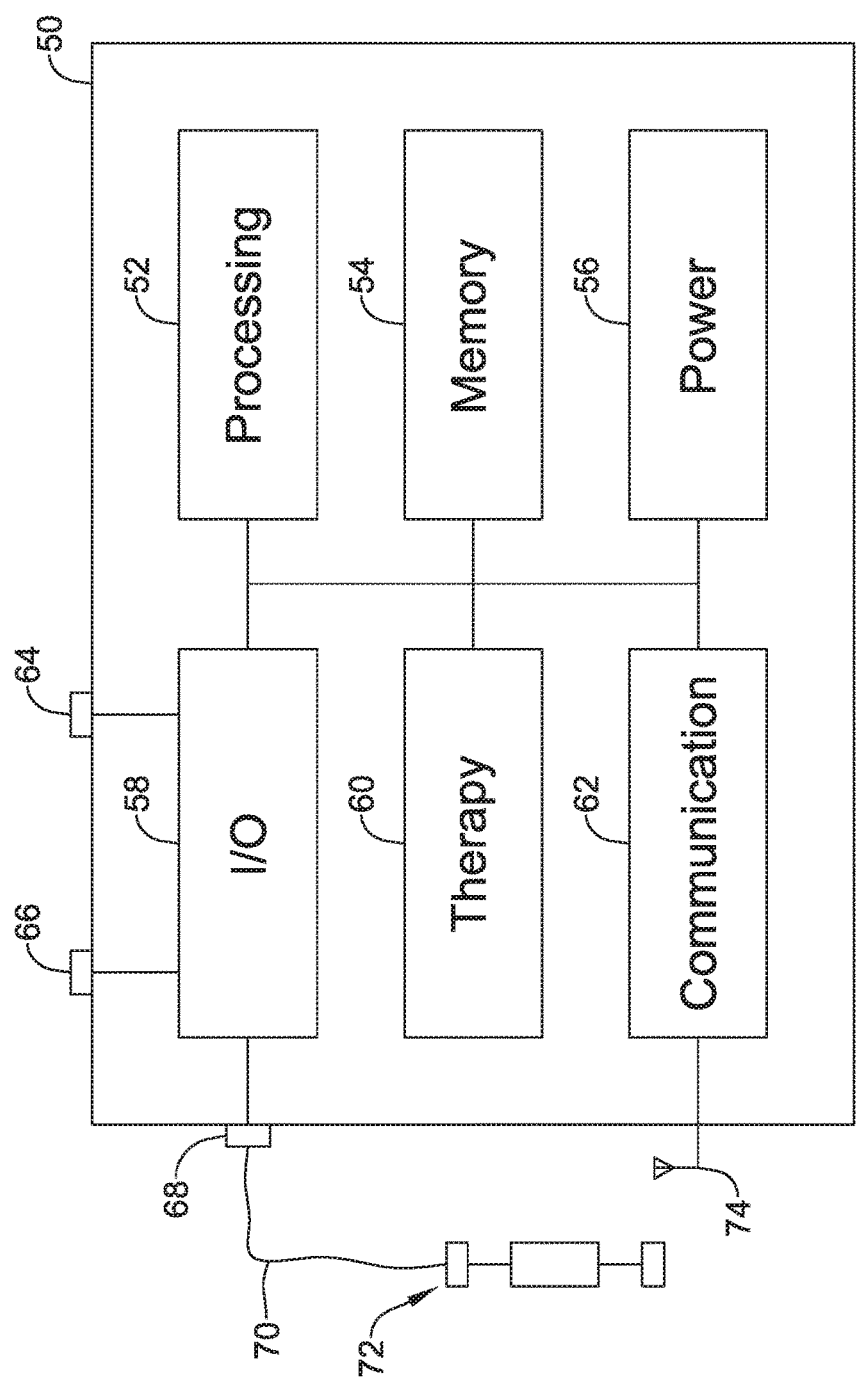
FIG. 2 illustrates a block diagram of an implantable medical device.

FIG. 2 illustrates a block diagram of an implantable medical device. The illustration indicates various functional blocks within a device 50, including a processing block 52, memory 54, power supply 56, input/output circuitry 58, therapy circuitry 60, and communication circuitry 62. The I/O circuitry 58 can be coupled to one or more electrodes 64, 66 on the device 50 housing, and may also couple to a header 68 for attachment to one or more leads 70 having additional electrodes 72. The communication circuitry 62 may be coupled to an antenna 74 for radio communication (such as Medradio, ISM, or other RF) and/or may couple via the I/O circuitry 58 to a combination of electrodes 64, 66, 72, for conducted communication.

The processing block 52 will generally control operations in the device 50 and may include a microprocessor or microcontroller and/or other circuitry and logic suitable to its purpose. Processing block 52 may include dedicated circuits or logic for device functions such as converting analog signals to digital data, processing digital signals, detecting events in a biological signal, etc. The memory block may include RAM, ROM, flash and/or other memory circuits for storing device parameters, programming code, and data related to the use, status, and history of the device 50. The power supply 56 typically includes one to several batteries, which may or may not be rechargeable depending on the device 50. For rechargeable systems there would additionally be charging circuitry for the battery (not shown).

The I/O circuitry 58 may include various switches or multiplexors for selecting inputs and outputs for use. I/O circuitry 58 may also include filtering circuitry and amplifiers for pre-processing input signals. In some applications the I/O circuitry will include an H-Bridge to facilitate high power outputs, though other circuit designs may also be used. Therapy block 60 may include capacitors and charging circuits, modulators, and frequency generators for providing electrical outputs. For devices such as insulin and drug pumps the therapy circuit 60 may include a pump or pump actuator coupled to a delivery system for outputting therapeutic material, rather than using the I/O circuitry 58 as would be typical for systems that generate an electrical therapy output.

Communications circuitry 62 may include a frequency generator/oscillator and mixer for creating output signals to transmit via the antenna 74. Some devices 50 may include a separate ASIC for the communications circuitry 62, for example. For devices using an inductive communication output, an inductive coil may be included. Devices may also use optical or acoustic communication approaches, and suitable circuits, transducers, generators and receivers may be included for these modes of communication as well or instead of those discussed above.

As those skilled in the art will understand, additional circuits may be provided beyond those shown in FIG. 2. For example, some devices 50 may include a Reed switch or other magnetically reactive element to facilitate magnet wakeup or reset of the device by a user. Some systems may omit one or more blocks, for example, an implantable cardiac monitor can omit therapy block 60, and an LCP may exclude the header 68 for coupling to lead 70.

In several embodiments, the present invention is directed toward the management and optimization of conducted communication between two implanted medical devices. For example, an LCP may communicate with an SICD. The LCP may, for example, provide a detected heartbeat rate to the SICD in order to assist the SICD in making a therapy determination. In another example, the SICD may request status from the LCP or may direct the LCP to deliver pacing pulses.

Other combinations of systems may use conducted communication between implants for various reasons. For example, if a patient has both a drug pump and a spinal cord stimulator, the drug pump may communicate to the spinal cord stimulator that it is in need of servicing, such that both systems may use their internal annunciating mechanisms to alert the patient that the drug pump requires service. As integrated systems develop, it may become possible to develop simplified devices that omit, for example, standard telemetry or annunciator circuits, and instead use conducted communication to another implant that includes full telemetry and annunciator circuits. If telemetry and/or annunciator circuits are omitted in one or more devices, the devices may become smaller and power consumption may be reduced. Thus conducted communication optimization may facilitate development of smaller and/or longer lasting devices in addition to facilitating inter-device coordination for therapy purposes.

Figure 3:
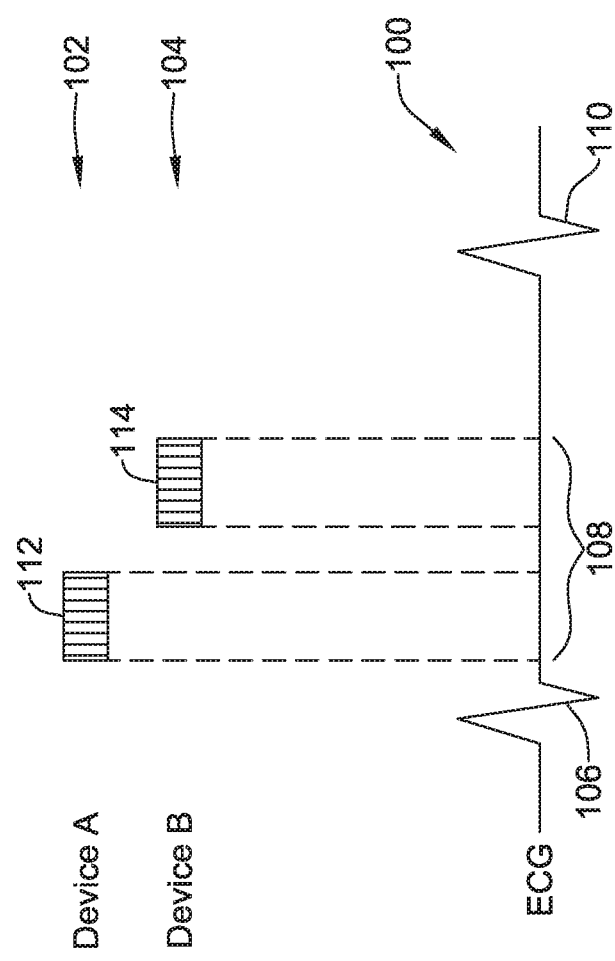
FIGS. 3-5 are diagrams illustrating communications signals relative to biological signals.
Figure 4:
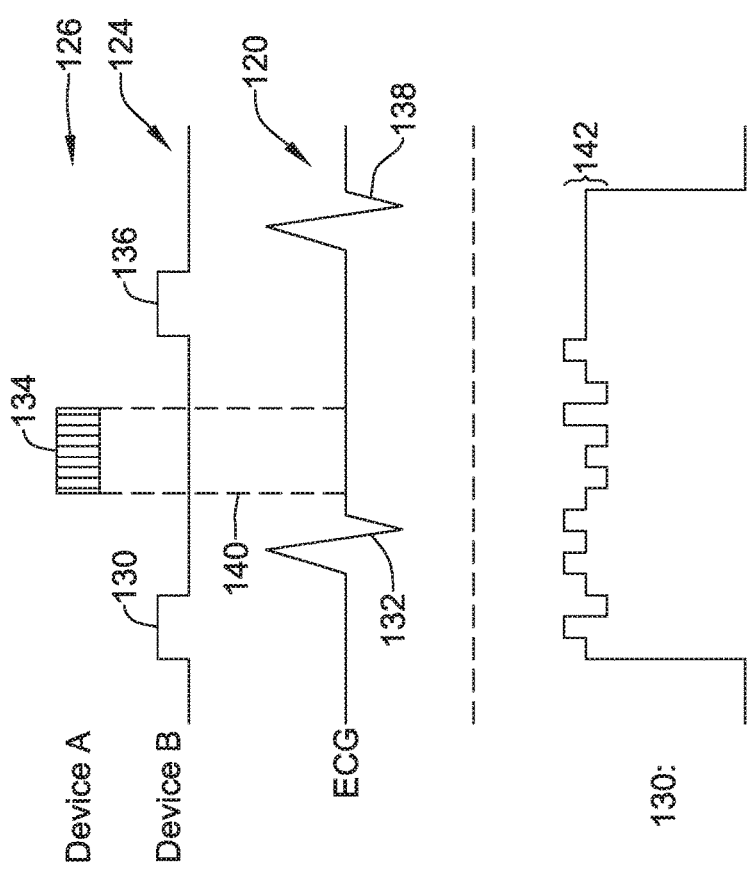
Figure 5:
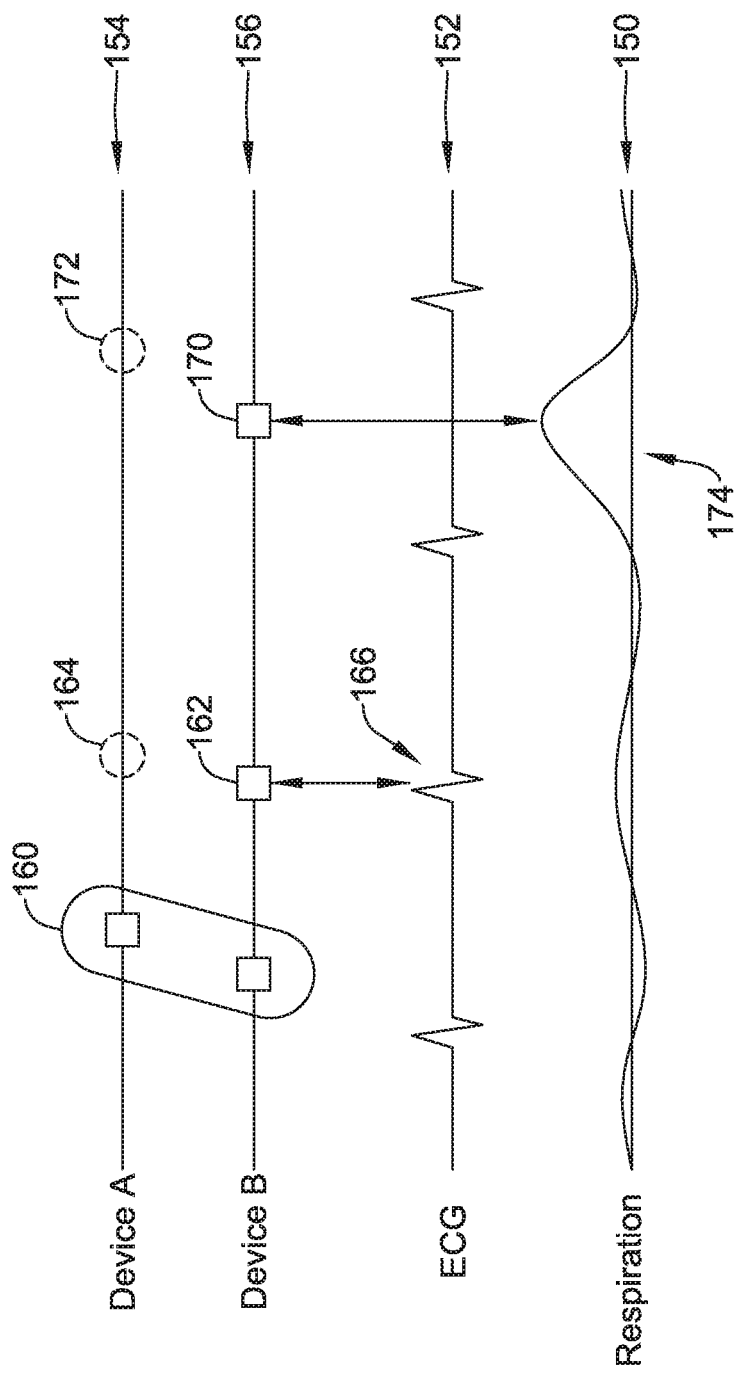

FIGS. 3-5 are schematic diagrams illustrating communications signals relative to biological signals. Conducted communication takes place within the body, and so it is subject to interference from various biological functions. Respiration and the cardiac cycle are two particular biological functions of interest, though any other biological function, cyclic or not, may also be addressed using the methods and devices herein.

FIG. 3 illustrates an ECG signal at 100, and communications by Device A at 102 and Device B at 104. The ECG shows a QRS complex (a heartbeat) at 106 followed by an interval 108, and another beat at 110. In this illustration, Device A sends a data packet 112 during the interval between beats 106, 110, and Device B responds with a packet at 114. The phrase "data packet" is used for convenience and should be understood as generically including any type of message/frame structure; no particular structure, type of data, size or other meaning should be implied.

In FIG. 3, the communication packets are shown as being sent independent of therapy output by either Device A or Device B. FIG. 4 shows another scheme in which Device B is configured to embed communications in a therapy output. The ECG is shown at 120, and the therapy output of Device B is shown at 124, while the communications from Device A are shown at 126. The therapy output 124 includes pacing pulses 130 and 136, which trigger beats 132 and 138 respectively on the ECG 120.

A detail view of pacing pulse 130 is shown below, and it is seen at 142 that the shape of the pacing pulse 130 includes amplitude modulation embedding a data packet. Other approaches to embedding information in a pacing pulse can be used; the illustration is simplified in FIG. 4 since the present invention is not limited to any specific manner of embedding data.

In the example of FIG. 4, Device A is designed to recognize the data 142 embedded in the pacing pulse 130. In this example, Device A responds with a data packet at 134 following the end of the QRS complex of beat 132. In an alternative, Device A could sent data packet 134 and Device B would respond with a message embedded in pacing pulse 136. Preferably, the embedded data 142 does not affect the effectiveness of therapy of the pacing pulse 130.

The signals for conducted communication are generally intended to have amplitudes that will not cause cardiac or skeletal muscle contraction, with the exception of the case in which the conducted communication is embedded in a stimulus signal, such as pacing pulse 130 with data 132 in FIG. 4. Typically, the patient should not be aware of the conducted communication signal. In FIG. 4, the amplitude, duration and/or frequency content of the data packet 134 would be selected to avoid stimulating muscle (skeletal or cardiac). Delivery of the data packet 134 during the QRS complex 132 could cause Device B to miss the signal or interpret it as part of the QRS complex 132. Therefore, as indicated at 140, the data packet 134 is intentionally delivered after the conclusion of the QRS complex for beat 132. Meanwhile, the data packet 134 must also terminate prior to delivery of the next pacing pulse 136.

While the illustration of FIG. 4 suggests avoidance of the QRS complex, some examples may not include such avoidance. For example, communication may be delivered using pulse widths which will allow receiving circuitry to distinguish the QRS complex from a conducted communication signal by the use of high pass filtering, since the QRS complex generally comprises signal frequencies below 40 Hertz. Some examples of optimization of communication relative to a biological signal such as the QRS complex are shown in U.S. Provisional Patent Application No. 62/134, 752, titled COMMUNICATIONS IN A MEDICAL DEVICE SYSTEM WITH TEMPORAL OPTIMIZATION, filed on Mar. 18, 2015, the disclosure of which is incorporated herein by reference.

FIG. 5 illustrates a scenario in which multiple biological signals interact with and potentially impair communication. A signal representative of the impact of respiration is shown at 150, as well as an ECG signal at 152 and communication for Device A at 154 and Device B at 156. At 160 a combination of communication signals are shown for Device B with a response from Device A. These communications take place after a QRS complex on the ECG. However, a later communication from Device B at 162 is not acknowledged at 164 by Device A, possibly due to the interference of the ECG 152 having a QRS complex at 166. Later, at 170, Device B again tries to communicate, however, the respiration signal at 174 interferes. The respiration signal 174 may represent a temporary change in transthoracic impedance or a motion artifact as the patient's chest moves, for example.

Other factors may come into play as well. For example, referring to FIG. 1, if two electrodes are placed on the ends of the LCP 16 in an orientation that is orthogonal to the electric field of a conducted communication that is sent to the LCP, the LCP may not "see" the signal, as the sensing electrodes on the LCP would be at equipotential relative to the incident electric field. If so, there would be a handful of potential mitigations including repositioning the LCP, selecting a different pair of electrodes on the LCP (if available) for receiving the signal, and selecting a different set of electrodes for sending the signal to the LCP from the SICD, for example. Thus, there are several factors that can affect the success of communication attempts.

Figure 6:
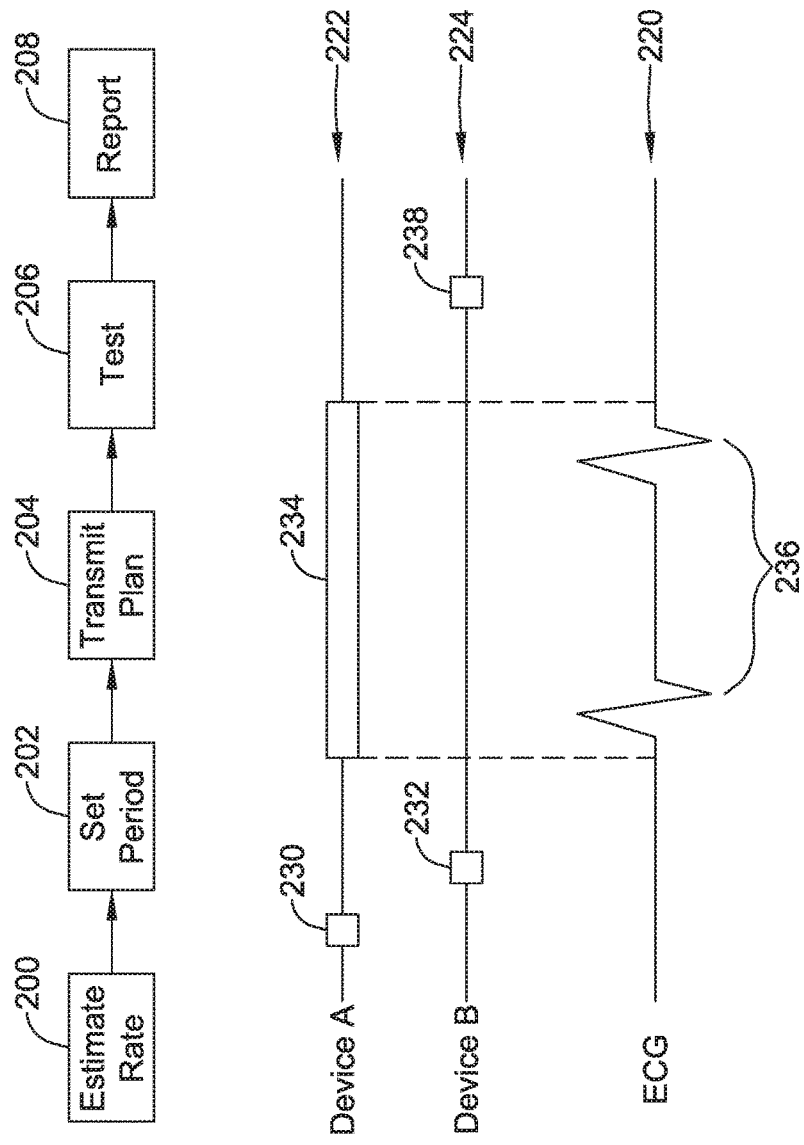
FIG. 6 illustrates a flow diagram and graphic for an illustrative method.

FIG. 6 illustrates a flow diagram and graphic for an illustrative method. In the method of FIG. 6, a testing regimen is put into place to identify and analyze potential interference sources. In the example, a rate estimate is made at 200. For this example, the ECG is the interference source under test, and so the "rate" is the cardiac beat rate, which can be determined in several ways including, for example, determining the period at which cardiac cycles occur by identifying R-waves, QRS complexes or other known recurrent parts of the cardiac cycle.

Using the estimated rate from 200, a period is set at 202, in which the period is selected to exceed a biological cycle. Here, the period would be chosen as the inverse of the cardiac beat rate plus, optionally, an additional margin. Optionally, one of the devices involved in the test may then transmit the testing plan at 204 to the other device(s) in the test. For example, if the system involved includes an SICD, an LCP, and an external programmer, either the SICD or LCP may provide the rate to the external programmer (or, if equipped for the task, the external programmer may calculate a rate). Then the external programmer may communicate a testing plan to each of the implanted devices at 204, in which the period to be used would be sent, along with an instruction to perform a conducted communication test.

In another embodiment, the external programmer can be omitted, and the SICD may provide a plan to the LCP, or the LCP may provide a plan to the SICD. Alternatively, a plan may not need to be conveyed. As shown below, the test will involve delivering a relatively long-duration communication output; the receiving device may be equipped to identify the long-duration communication output as a test mode, and simply wait for the communication output to terminate. The communication of a plan 204 is not necessary but may be helpful for the receiving device of a test communication output to determine that it is not being subjected to an external noise, for example.

Next the test is performed as shown at 206. The test sequence is shown graphically, with the ECG shown at 220, communication outputs of Device A shown at 222, and communication output of Device B shown at 224. In the test, Device A provides a communication packet at 230, which is acknowledged and responded to by device B at 232. This exchange 230/232 may include the optional test plan.

Next, a long-duration communication output is generated by Device A, as shown at 234. As highlighted at 236, the period for the long-duration communication output 234 is selected to exceed the length of a cardiac cycle. Optionally, during the long-duration communication pulse output 234, a pre-specified pattern of data may be communicated (for example, all "1s", all "0s" or a repeating 01010101 sequence). Device B listens for the output 234 and assesses communication metrics which may include, for example, amplitude, relative signal strength indicator (RSSI), signal-to-noise ratio (SNR), slew, frame error or bit error rate (BER), or others. By monitoring over time, the test method can determine how the ECG affects these communication metrics.

In one embodiment, a mapping can be generated by having the ECG 120 captured by one of the devices (either implant or the external programmer, depending on which are available) synchronized to the long-duration communication output 234. Such a mapping could indicate, for example, if the SNR, RSSI, or BER change depending on the state of the ECG. For example, the mapping may indicate if the BER increases or RSSI decreases during the QRS complex of the ECG.

Following the test, results can be reported at 208. For example, Device B may send a communication packet 238 to Device A containing data relating to the observed communication metrics. Such results can be exchanged between two implanted systems or may be sent to an external device (such as a programmer or smartphone) to enable configuration of system communication. A communication strategy may be formulated and redistributed among the devices in the system, if desired. Examples of strategy elements may include:

- timing of communication relative to a biological marker such as a transthoracic impedance peak, QRS complex, R-wave, other cardiac signal, respiration signal, or received artifact such as a motion artifact
- selection of or tiering of communication vectors if multiple vectors are available
- communication retry strategies including timing or other changes to be made with retries
- modifications to communication signal amplitude, data rate or other characteristic strategies for handling urgent versus non-urgent communications with respect to any of the above Any of these elements may be integrated into a communication strategy for the system.

Figure 7:
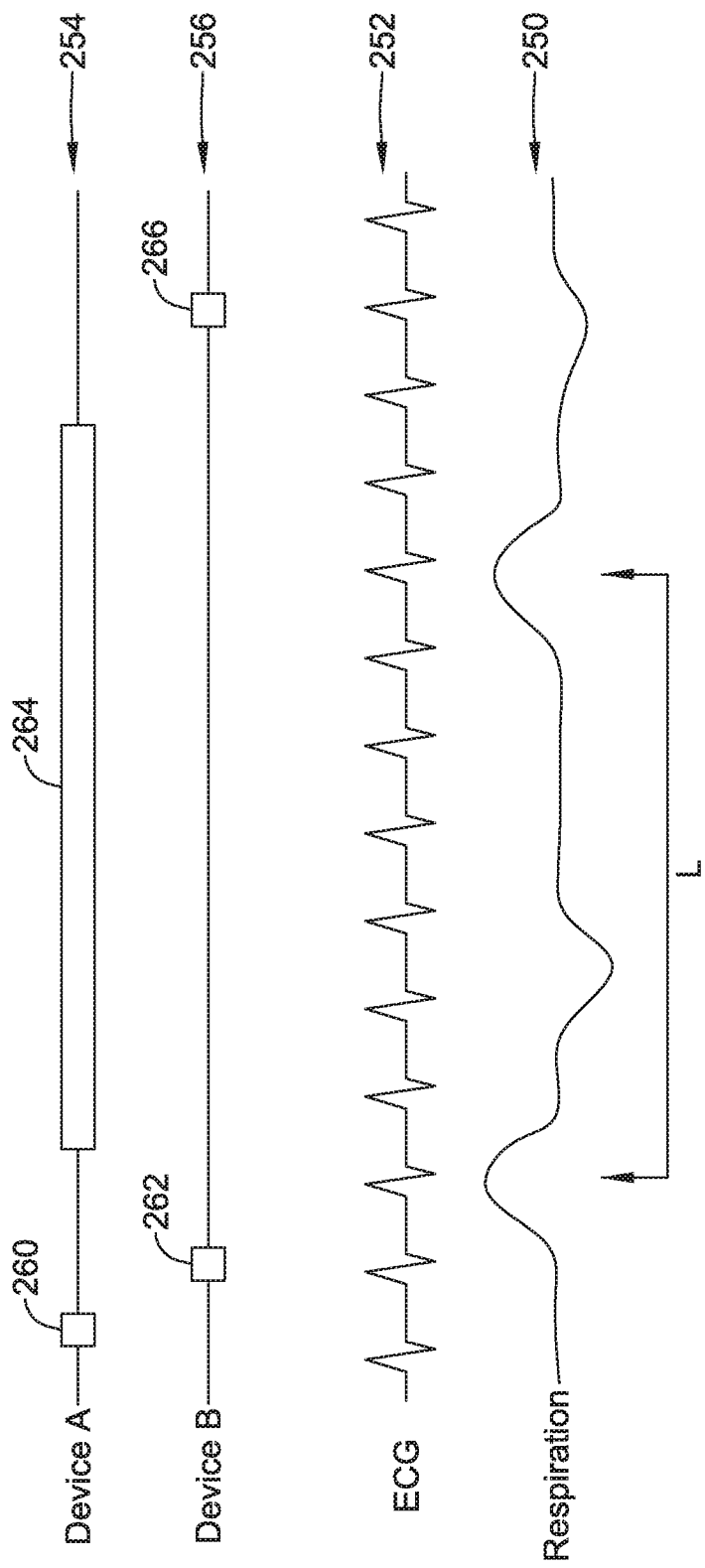
FIGS. 7 and 8 are diagrams illustrating communications signals and test signals relative to biological signals.
Figure 8:
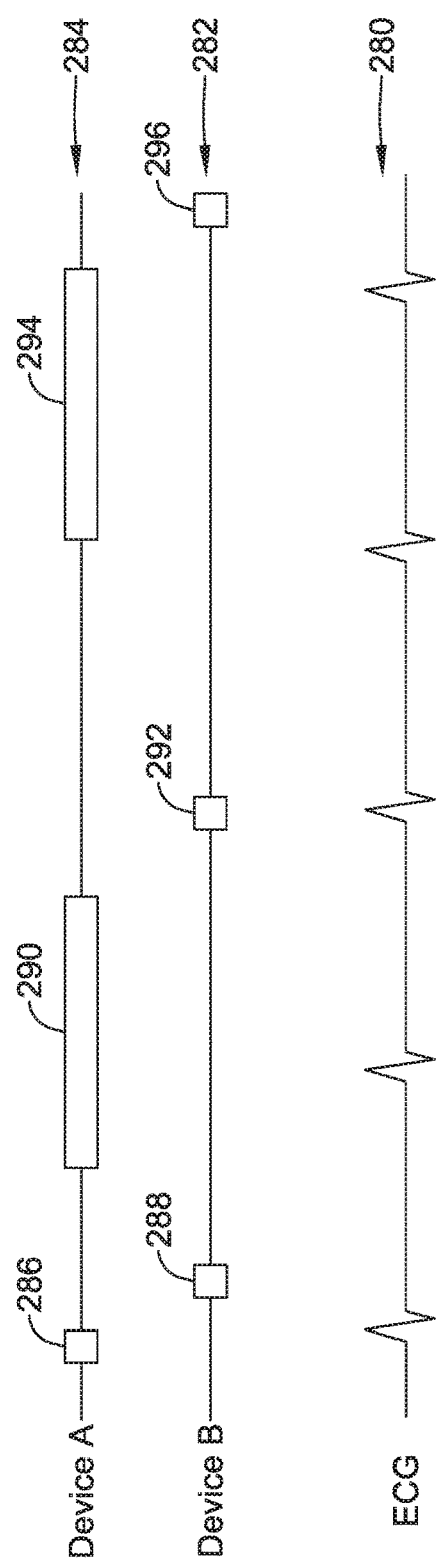

FIGS. 7 and 8 are diagrams illustrating communications pulses and test signals relative to biological signals. Referring first to FIG. 7, the represented signals include a signal representative of respiration 250, the ECG 252, Device A 254, and Device B 256. Optionally, Device A issues a communication at 260 requesting a test sequence, and Device B provides a response at 262 acknowledging, approving, and indicating a period to use in the communication. Device A then issues a long-duration communication signal at 264, this time being of a duration sufficient to capture a full respiration cycle, L, plus some margin, delta. Device B observes the signal 264 and one or more metrics of the communication quality and may communicate such information in packet 266 either back to Device A or to an external programmer. A mapping of the received communication characteristics can be generated using the information captured by Device B, and referencing one or both of the Respiration signal 250 or ECG 252.

FIG. 8 illustrates an example in which multiple communication configurations can be tested. ECG is shown at 280, and communication behavior of Device A at 284 and Device B at 282. Here, Device A sends a first packet at 286 to request and/or provide parameters for an upcoming test, and Device B provides acknowledgement and/or parameters at 288. A first test is provided at 290, spanning at least one cardiac cycle as illustrated by the ECG 280. Device B acknowledges the end of the first test 290 with a response at 292. This acknowledgement 292 may indicate a need for further testing, if desired. Device A then reconfigures itself by, for example, selecting a different communication vector, increasing or decreasing signal power or data rate, or adjusting a data format or frequency for communication. A second test occurs at 294, again overlapping an entire cardiac cycle as shown in the ECG, and device B provides an acknowledgement and test data at 296.

In an alternative, in the arrangement of FIG. 8, the communication 292 between tests by Device B may indicate a difficulty receiving the first test signal 290, and instructions to reposition Device A or Device B may be provided. Once the repositioning is completed, then the second test signal 294 can be generated. Additional intervening data packets may be provided by one or both of Devices A, B, or an external programmer, to facilitate retest.

In another alternative, the first test signal 290 may be provided while a patient is assuming a first posture, for example, the patient may be supine, prone, seated or standing. The second test signal 294 may be provided with the patient in a different posture. In this manner, the possible impact on communication success of relative movement and/or reorientation of Device A and Device B due to postural changes can be tested.

The system may be configured to use a communication plan that adjusts a communication configuration to account for posture changes. To accommodate a postural plan for communication, one or more implanted devices may include an accelerometer, piezoelectric device, or other feature to allow identification of the patient's posture and to accommodate any modification of communication that would be taken in response. For example, a device may have an accelerometer allowing tracking of the patient's posture between at least first and second states. If testing shows that the first state is suited to a first communication configuration, while the second state is suited to a second communication configuration, the device may switch communication configurations when a detected change from the first state to the second state occurs.

FIGS. 9-10 are flow diagrams for illustrative methods. In FIG. 9, as shown at 300, a first test is performed using a first communication vector, and a second test is performed at 302 using a second communication vector. A report is generated at 304, and the communication vector for default use is selected at 306.

FIG. 10 provides another example. Here, an implant procedure is begun at 320 for example, for an LCP. One or more communication vectors may be tested at 322 using for example an SICD, and the position/orientation of the device being implanted can then be adjusted as noted at 324. For example, with an LCP, the position of the LCP on the cardiac wall may be adjusted, or the LCP may be rotated. As indicated at 326, with the new orientation a retest may be performed.

For example, in an SICD/LCP combination system, the SICD may be implanted first. The LCP can be advanced to the right ventricle, but remain un-fixated, or fixated but not released, by the delivery catheter. A test mode can then be called for the SICD and LCP to check on communication signals between the SICD/LCP. The two implants may do all the work themselves, or an external programmer may be used to gather data from either or both. If desired, an external programmer may communicate with the LCP either by conducted communication or by virtue of continued coupling to the delivery catheter (that is, connected communication) may provide a feedback signal (audible or visual, for example) relating to the communication quality during the implant. The implanting physician may adjust the implant position, communication sensitivity or power level of the LCP prior to fixation or release to ensure good communication between the LCP and the SICD. The physician may also adjust settings of the SICD. The feedback signal may be provided in real-time, if desired, that is, as measurement readings are generated by one of the implanted devices, those readings can be communicated to the external programmer and displayed to the user.

In one example, a first implant monitors conducted communication signals received from a second implant using a first pair of electrodes, and generates an output communication using a different, possibly orthogonal, pair of electrodes (for conducted communication) or an antenna or inductive element (for RF or inductive communication) for receipt and display by an external programmer as measurements are made. FIG. 11 illustrates an example.

In FIG. 11, the conducted communication of Device A is shown at 330, a first communication channel for device B is shown at 332 as B(1), and may in this example be conducted communication, a second communication channel for Device B is shown at 334 as B(2) and may represent any of connected, conducted, RF, optical, acoustic, or inductive communication, and the ECG is shown at 336. As with other examples, Device A and Device B optionally exchange messages 340, 342 relating to an impending long-duration test pulse 344 that is intended to span a biological cycle such as that on the ECG. During the test pulse 344, Device B issues a number of data packets 348 which may be intended for receipt by another implanted device, by an external programmer, or by Device A, which may include at least two communication channels as well.

In one example, Device B is an LCP having sufficient electrodes to have two spatially diverse (such as orthogonal) conducted communication channels, while Device A is an SICD having sufficient electrodes disposed on the torso of the patient to support at least two spatially diverse (such as orthogonal) conducted communication channels. In an alternative, Device A and Device B can communicate using one mode of communication on a first channel and a second mode of communication on a second channel. In another example, a higher power communication mode (RF, for example) is used during testing of a lower power communication mode (conducted communication).

Figure 12A:
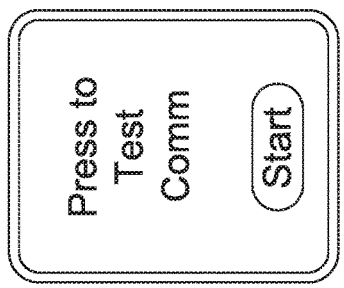
FIGS. 12A-12E show programmer screens for an illustrative method.
Figure 12B:
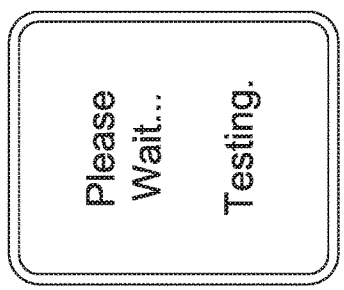
Figure 12C:
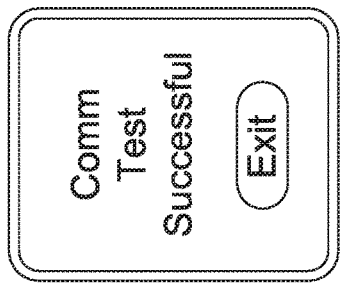
Figure 12D:
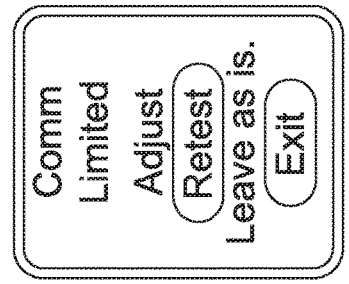
Figure 12E:
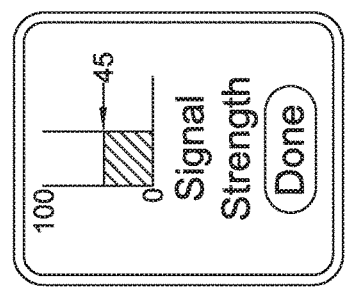

FIGS. 12A-12E show programmer screens for an illustrative method. The test method can begin with the programmer screen in FIG. 12(A), instructing the user to press start to begin testing. The testing then takes place with a "wait" screen illustrated in FIG. 12(B); a status or progress bar may be provided as well. FIG. 12(C) illustrates a screen indicating that the communication testing was successful, with an exit button. FIG. 12(D) shows a screen indicating that the communication testing was unsuccessful or marginally successful and communication ability is limited. The user is presented the opportunity to adjust the system setup, which may include repositioning one or more devices/electrodes, or may include changing a setting in one or more devices either as directed by the user or by following an adjustment/retest protocol. If the user elects, the setup may be left as-is, with limited inter-device connectivity by selecting the Exit button. FIG. 12(E) shows a real-time feedback screen which may indicate to the user the status of the communication link during adjustment of device positioning. For example, if an LCP is being implanted, the signal strength of conducted communication with another implanted device can be displayed on the programmer screen while the implant is taking place. As an alternative, audible tones or other indicator can be provided, in place of or in addition to a visible indication on the programmer screen.

FIG. 13(A) illustrates a testing setup for implanted systems with an external programmer. The external programmer is shown at 350 with a pair of surface electrodes 352, 354, and a telemetry wand 356. An SICD is shown at 360 with a lead extending to electrodes 362, 364, and 366, with the canister housing the SICD also being an electrode. An LCP is shown at 370, and in the detail view of FIG. 13(B), includes electrodes 372, 374, 376, 378. In the configuration shown, the LCP 370 may engage in conducted communication with the surface electrodes 352, 354 of the programmer 350, as well as with the housing and lead electrodes 362, 364 and 366 of the SICD 360.

Thus, in one example, the LCP could use electrodes 374, 378 as opposing poles for conducted communication with the surface electrodes 352, 354 of the programmer 350, while also using electrodes 372, 376 as opposing poles for conducted communication with electrode 364 and the housing of the SICD, to allow for real-time monitoring of communication qualities to the programmer 350 for display to a user. In another example, the LCP could generate a conducted communication output using electrodes 372, 376 for receipt by electrodes 362, 366 of the SICD 360, which in turn can provide real-time data on conducted communication via an antenna (not shown) for RF telemetry to the wand 356 and programmer 350 for display to a user. In yet another example, the LCP may receive conducted communication using electrodes 372, 376 from the housing and electrode 364 of the SICD, while sending data packets to the SICD using electrodes 374, 378 for receipt by electrodes 362, 366. Other configurations and combinations may also be used.

Figure 14:
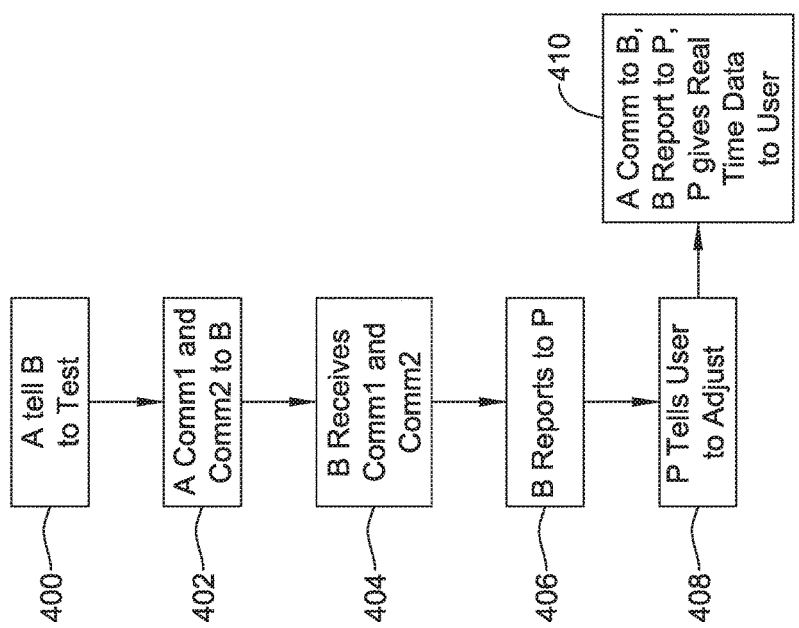
FIGS. 14-16 are flow diagrams for additional embodiments.
Figure 15:
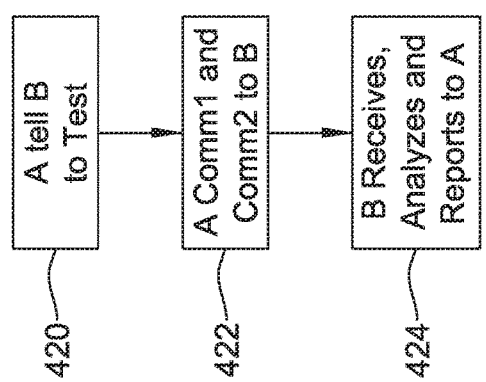
Figure 16:
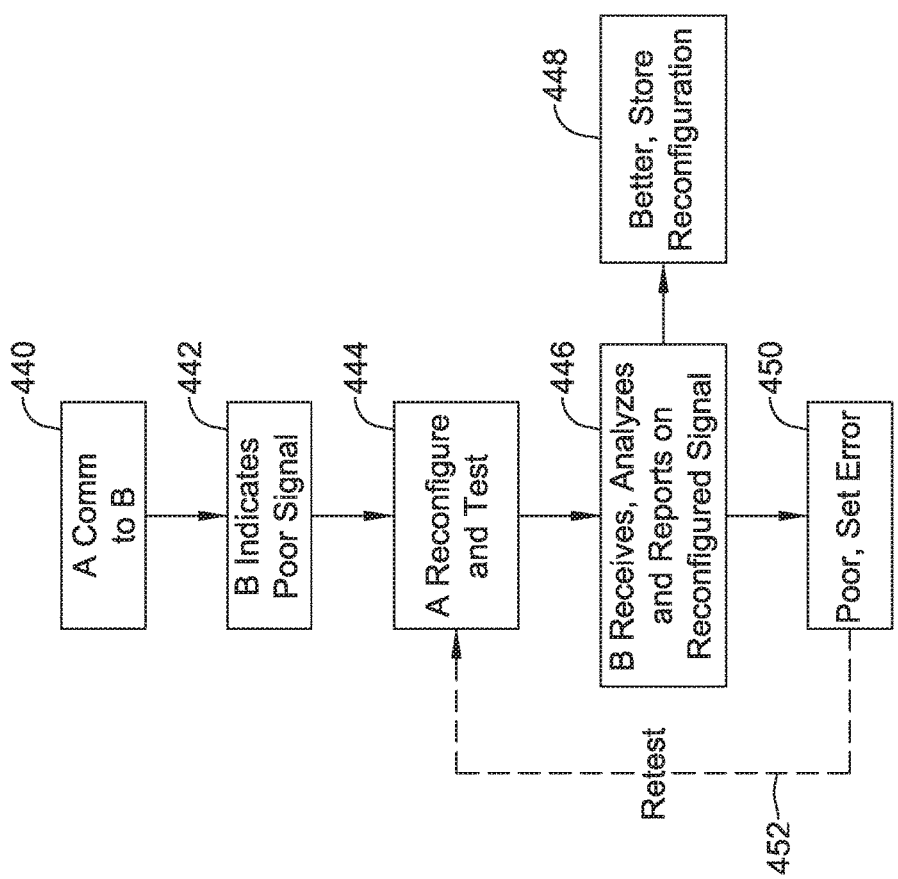

FIGS. 14-16 are flow diagrams for additional embodiments. In FIG. 14, the testing process begins with Device A telling device B that a test of conducted communication is going to occur at 400. Next, device A issues first and second communications to device B as indicated at 402. Device B receives the first and second communications as indicated at 404. Finally, Device B reports the results of the test to an external programmer, P, as indicated at 406, providing one or more of a preference between the first and second communication attempts and/or communication metrics such as signal strength, signal-to-noise ratio or bit error rate, for example. Optionally, P may provide a message to a user/physician to adjust positioning of one or more implanted devices, as shown at 408. Also, optionally, device A may again communicate one or more data packets to device B to provide real-time feedback to the physician, at 410. If desired, the entire method may be replaced by block 410 alone, in which case the real-time feedback may be provided for each communication test. Though not shown, the programmer P may also issue commands to device A to implement a specific configuration of conducted communication.

In FIG. 15, again, device A may indicate to device B that communication testing is to occur, as shown at 420. Next, device A issues first and second communication messages, as shown at 422. Finally, device B receives and analyzes the communications from A, and issues a report to Device A, as indicated at 424.

In FIG. 16, the initial message from Device A to Device B indicating that testing is to take place may be omitted. Instead, the method begins with Device A communicating to Device B, as shown at 440. Next, device B provides an indication that a poor signal was received, as shown at 442. Device A may then reconfigure itself and perform a conducted communication test, as shown at 444. In response to the test, device B provides a report on the communication quality for the reconfigured device A, as shown at 446. If the reconfiguration resulted in better quality sufficient to meet the system needs, then the reconfiguration can be stored in Device A and used as a new default configuration. Otherwise, if the communication quality does not improve, Device B may set an error flag and communicate such an error to Device A, as indicated at 450, in addition to or as an alternative for performing a retest 452.

If desired, one or more therapy or other modes for either of Device A or Device B may be disabled in conjunction with the error flag at 450. For example, if Device A is an SICD, and device B is an LCP, and the SICD is set up to command antitachycardia pacing (ATP) by the LCP using conducted communication, the setting of the error flag at 450 may suspend the ability of the SICD to command ATP.

Following are a number of additional illustrative examples which should be viewed as providing additional examples and not as limitations on the invention.

A first non-limiting example is an implantable medical device comprising means for communicating by conducted communication with at least a second implantable medical device, in which the means for communicating may include the I/O circuitry 58 of FIG. 2 along with the electrodes 64, 66 and/or 72, as controlled by the processing circuitry 52 and/or powered by therapy circuitry 60. The first non-limiting example further includes means for setting the communication module into a continuing receive mode for analyzing a first signal received from the second implantable medical device and a second signal received from the second implantable medical device, where the means for setting may comprise the processing circuitry 52 using embedded instructions or an instruction set from memory 54 which is configured to perform in the manner described relative to testing Device B in FIG. 8 (receiving signals 290 and 294, for example), and/or the manner described relative to blocks 300 and 302 of FIG. 9. This first non-limiting example may further comprise means for analyzing the first signal and the second signal as received by the means for communicating which may include the I/O circuitry 58 of FIG. 2 using dedicated circuitry or operating in concert with the processing circuitry 52 of FIG. 2 (and memory 54) to generate analytics such as amplitude, relative signal strength, signal-to-noise ratio, slew, and frame or bit error rate; the means for analyzing may further include input circuitry for analyzing a biological signal including, for example, an ECG or EGM analyzer, skeletal or diaphragm muscle signal analyzer, an accelerometer, a pressure sensor, a microphone for observing sounds such as heart sounds, a blood analyte sensor, or a surrogate of a biological signal such as a thoracic impedance monitor, etc. Finally the first non-limiting embodiment may comprise means for generating an output communication indicating a result of the analysis of the first signal and the second signal, wherein the means for generating an output may comprise the processing circuitry 52 of FIG. 2 making use of one of conducted communication circuitry including the I/O circuitry 58 and electrodes 64, 66, and/or 72, or the communication circuitry 62 and antenna 74, which may perform as shown in block 208 of FIG. 6, or block 304 of FIG. 9, or block 406 of FIG. 14, or block 424 of FIG. 15, and associated text.

A second non-limiting example takes the form of an implantable medical device comprising means for communicating by conducted communication with at least a second implantable medical device in which the means for communicating may include the I/O circuitry 58 of FIG. 2, as controlled by the processing circuitry 52 and/or powered by therapy circuitry 60 where the processing circuitry may use embedded instructions or instructions stored in memory 54. The second non-limiting example further includes at least first, second and third electrodes (such as electrodes 64, 66 and/or one or more of the electrodes at 72), configured for conducted communication with the second implantable medical device such that at least first and second conducted communication vectors are available for use by the communication means. The second non-limiting example further includes means for setting the means for communicating to a continuing transmit mode for using the first conducted communication vector to generate an output, and then using the second conducted communication vector to generate an output, the means for setting including at least the I/O circuitry 58 of FIG. 2, as controlled by the processing circuitry 52 and/or powered by therapy circuitry 60, where the processing circuitry may use embedded instructions or instructions stored in memory 54, which may perform as shown in FIG. 8 (with communications 290 and 294) or in accordance with blocks 300 and 302 of FIG. 9, or block 402 of FIG. 14, or block 422 of FIG. 15, as well as associated text. The second non-limiting example further includes means for determining, from information provided back to the implantable medical device, which, if any, of the first conducted communication vector and second conductive communication vector is to be used for delivering conducted communication messages to the second implantable medical device, which means may include the processing circuitry 52 and/or powered by therapy circuitry 60, where the processing circuitry may use embedded instructions or instructions stored in memory 54, which may perform as noted at block 304 of FIG. 9, or blocks 404/406 of FIG. 14, or block 424 of FIG. 15, as well as associated text. Finally the second non-limiting embodiment may include means for setting a default conducted communication vector for use by the means for communicating, the processing circuitry 52 and/or powered by therapy circuitry 60, where the processing circuitry may use embedded instructions or instructions stored in memory 54 and may perform the steps as noted by block 306 of FIG. 9 and associated text.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A method of performing a diagnostic test in an implantable medical device system comprising:
   generating a first conducted signal from a first medical device intended for receipt by a second medical device comprising an output pattern for a selected period;
   receiving the conducted signal by the second medical device and calculating a first communication metric of the first conducted signal as received;
   wherein the selected period exceeds an expected or detected length of a recurring biological cycle.

2. The method of claim 1 wherein the recurring biological cycle is a cardiac cycle.

3. The method of claim 1 wherein the recurring biological cycle is a respiration cycle.

4. The method of claim 1 wherein the first medical device comprises at least three electrodes configured to output a conducted signal and the first conducted signal is generated by a first combination of electrodes, the method further comprising generating a second conducted signal using a second combination of electrodes, receiving the second conducted signal and calculating a second communication metric for the second conducted signal.

5. The method of claim 4 further comprising comparing the first communication metric as calculated for the first conducted signal as received to the second communication metric as calculated for the second conducted signal.

6. A method comprising performing the method of claim 1 while a patient assumes a first posture, and repeating the method of claim 1 while the patient assumes a second posture.

7. The method of claim 1 wherein the first and second medical devices are each leadless cardiac pacemakers.

8. The method of claim 1 wherein the first medical device is a subcutaneous implantable defibrillator and the second medical device is a leadless cardiac pacemaker.

9. The method of claim 1 wherein the first medical device is a leadless cardiac pacemaker and the second medical device is a subcutaneous implantable defibrillator.

10. The method of claim 1 wherein the communication metric comprises one or more of amplitude, relative signal strength indicator, signal-to-noise ratio, slew, frame error, or bit error rate.

* * * * *